United States Patent [19]

Kelly, Sr.

[11] 4,214,317
[45] Jul. 29, 1980

[54] PROTECTIVE APPAREL

[76] Inventor: Thomas E. Kelly, Sr., 14202 Baldwin Mill Rd., Baldwin, Md. 21013

[21] Appl. No.: 8,883

[22] Filed: Feb. 2, 1979

[51] Int. Cl.³ .......................... A41D 13/08; A61F 9/06
[52] U.S. Cl. ................................................. 2/2; 2/11;
2/16; 2/59; 2/161 R; 51/270; 175/211; 408/67
[58] Field of Search .................... 2/2 R, 11, 16, 51, 59,
2/160, 161 R; 175/211; 408/67, 72; 51/268,
270; 144/252; 145/116 A

[56] References Cited

U.S. PATENT DOCUMENTS

| 375,958 | 1/1888 | Skeffington | 2/59 X |
|---|---|---|---|
| 890,088 | 6/1908 | Overshiner | 2/59 |
| 1,370,933 | 3/1921 | Torkelson | 2/11 |
| 1,742,331 | 1/1930 | Voigt | 51/270 |
| 1,981,570 | 11/1934 | Price | 175/211 |
| 2,497,749 | 2/1950 | Wagner | 2/16 |
| 2,941,214 | 6/1960 | Michael | 2/161 R |
| 3,339,435 | 9/1967 | Heitz | 408/67 |
| 3,570,009 | 3/1971 | Spruell | 2/16 |
| 3,583,821 | 6/1971 | Shaub | 408/72 R |
| 3,934,661 | 1/1976 | Sauerwein et al. | 175/211 |

FOREIGN PATENT DOCUMENTS 5914 of 1913 United Kingdom ...................... 175/211

Primary Examiner—Louis Rimrodt
Attorney, Agent, or Firm—John F. McClellan, Sr.

[57] ABSTRACT

An article of apparel for shielding portions of the body from flying debris such as saw splinters, drill chips, dust, grit, and other particulate matter resulting from overhead work with a hand-held tool, includes a sleeve with an arm-fitting cuff for containing one hand of a user, a porous sleeve-section connecting with the cuff, a transparent sleeve section connected above the porous sleeve section and a loop with a downward angled handle for grasping by the other hand of a user and supporting the upper end of the sleeve against an overhead; pumping action of sawing or the like is prevented by breathing action of the porous sleeve section from blowing debris out of the sleeve, and the transparent sleeve section affords good visibility combined with shielding for the user.

5 Claims, 4 Drawing Figures

PROTECTIVE APPAREL

This invention relates generally to human apparel and specifically to apparel protective against debris during working. Workers drilling and sawing overhead as for installation of wiring receptacles, lights and fire detectors generate a quantity of particulate matter which falls into eyes and hair and the body generally and on rugs and floors below and is blown about the room, is tracked, and is often inhaled.

A principal object of this invention is to provide an article of apparel which both protects the user from flying debris resulting from work overhead and which collects such debris before it scatters and drops, while preserving clear vision of the work area and permitting the range of hand and arm motion necessary for using ordinary hand tools such as hand saws and electric hand tools.

In prior art various disclosures have been made which in some way may be pertinent including those of the following U.S. Pat. Nos.:

1,370,933 issued Mar. 8, 1921, discloses a transparent shield with screen portion and wrap-around structure for securance of a portion of an arm (a hand);

1,981,570 issued Nov. 20, 1934, discloses a dust collector for drills and the like, to be applied to the work around the tool being used;

3,339,435 issued Sept. 5, 1967, discloses a bellows type dust collector for mounting on a tool and engaging the work;

3,583,821 issued June 8, 1971, discloses a flexible transparent cup-shaped debris collector for mounting on a tool and contacting the work; and 3,934,661 issued Jan. 27, 1976, discloses another form of bellows-like collector.

Also in Class 2 at subclasses 2, 9, 11, 16 and 15 various disclosures relate to body-mounted debris-shields.

However, it is believed that none of the prior art teaches Applicant's invention or provides structure accomplishing the objects of the present invention as herein set forth.

Further objects of the invention are to provide an article as described which is lightweight and convenient to use, is economical to manufacture and inexpensive to purchase, which is reliable and durable, and which permits the user safely to use both hands while at the same time preventing spillage from overhead work and assuring good illumination and manual and visual access.

Still further objects are to provide an article as described which in embodiments protects the overhead from damage, and which folds for storage.

In brief summary given for cursive descriptive purposes only and not as limitation, the invention in preferred embodiment includes a sleeve which is worn with a close fit around a portion of a body such as wrist or arm to enclose the hand and extends upward from a loose flexible portion to an extender for holding the open upper end of the sleeve as a debris collector against an overhead with the other hand, and which provides both visual access and filter type ventilation for preventing blowing out of debris collected.

The above objects and advantages of the invention will become more readily understood on examination of the following description, including the drawings in which like numerals refer to like parts:

Figure 1:
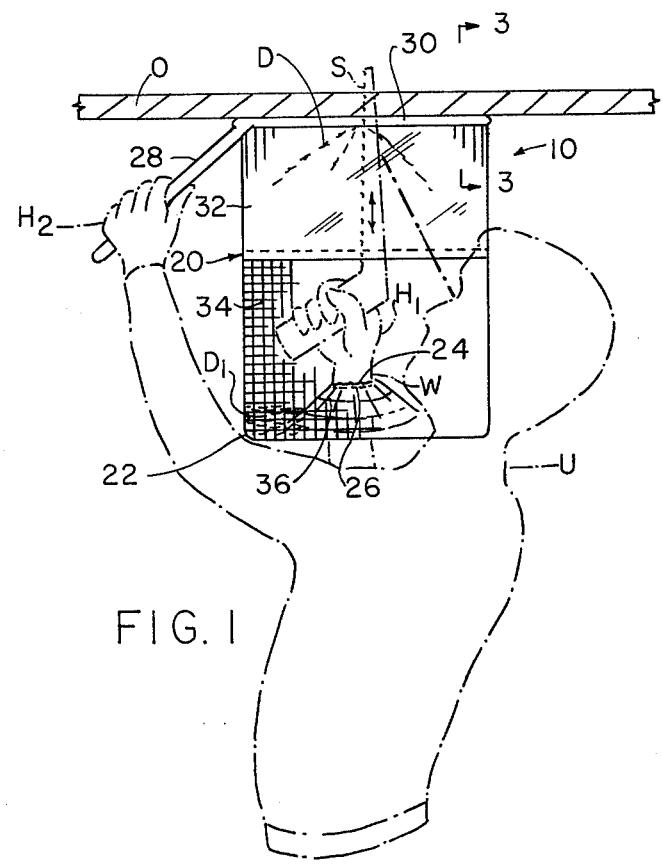
FIG. 1 is an elevational partially section depiction of the invention in use.

FIG. 1 shows the invention 10 in use as a user U saws a hole in an overhead O such as a plaster ceiling, using a coping saw S. The invention includes a special sleeve 20 which regardless of the force and nature of the flying debris D generated by the sawing, and regardless of the pumping action of the hand $H_1$ grasping and driving the saw, safely restrains and contains the debris in a pile $D_1$ at the bottom 22 of the sleeve. The bottom of the sleeve has an armhole 24 which is gathered, preferably by elastic 26, to fit snugly around the arm, preferably the wrist W, of the user, enclosing the tool-grasping hand in the sleeve.

The second or other hand $H_2$ of the user grasps a handle 28 which angles downwardly from attachment to a frame 30 which spreads the upper perimeter of the sleeve, and forces it flush against the overhead under the manual pressure.

The handle angle provides knuckle clearance, requires less reach, and permits easier insertion of the sleeve top portion into a refuse can, or the like, when desired to dump the sleeve contents.

Preferably, the body of the sleeve includes two tubular portions sewn or cemented end-to-end. The upper portion 32 preferably is of transparent material such as clear flexible polyester sheeting, providing clear visual access to the overhead area of operation from all angles around the point of operation. This permits more than one person to view the point of operation safely, and provides for all-sides illumination. Further, the flexibility permits storage in a small space.

The lower portion 34 preferably is of filter type material such as one or more layers of cheesecloth, or may be of other filter material such as porous cotton duck.

In operation, in the handsaw example illustrated, the user holds the frame against the ceiling, views through the transparent portion of the sleeve the area being sawed, and saws. Sawdust and splinters and plaster dust fall into the bottom of the sleeve; the porosity of the lower portion permits air to be pumped through the sleeve as result of the sawing reciprocation without blowing particulate material out through the lower portion or over the top between the frame and ceiling or otherwise scattering it.

Proportions of the sleeve may be about one foot (30 cm) in diameter, the frame being the same; the handle being aobut 9 inches (22.5 cm) long and inclined downward from the plane of the top of the frame about 30° to 45°; the transparent portion of the sleeve being about ⅓ the length. The length overall may be about 21 inches (52.5 cm); depending on intended use this may be longer or shorter but preferably is long enough to provide an upfold or return 36 on itself at the wrist, so that collected debris falls below the wrist in the return portion.

Figures 2, 3:
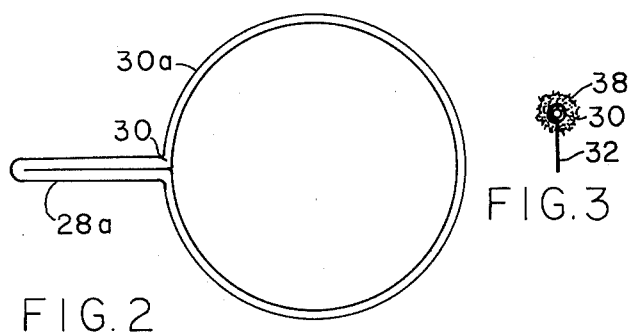
FIG. 2 is a plan view of one form of frame.
FIG. 3 is a sectional view adapted from 3—3, FIG. 1.

FIG. 2 shows that the frame 30 may economically be of one circle of wire or tubing with a circular portion 30a for the sleeve continuous with a compressed loop 28a for the handle, forming a generally pear-shape.

FIG. 3 illustrates in cross section another preferred provision of the invention, a cushion 38 which may be of terry cloth towelling material or other soft bulky, low friction material, wrapped around the top of the frame 30 to prevent wear and marking, and to assure a seal against the overhead regardless of local irregularities. To secure this, it may be looped around the frame and sewn at the lower edges and can help reinforce the plastic sheeting 32 which may be similarly attached.

Figure 4:
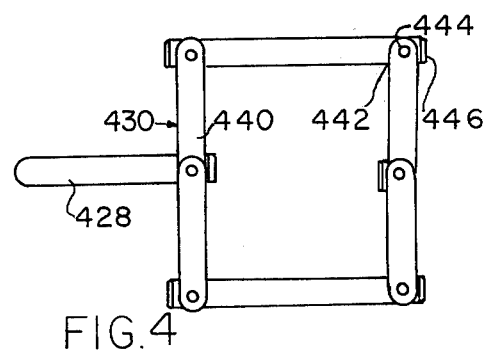
FIG. 4 is a plan view of another form of frame.

FIG. 4 shows another form of frame 430 which can have the sleeve attached as previously indicated, but can fold by means of pivot structure at the respective corners and midway two of the legs 440, the handle 428 being attached at one of the midway points. The pivot structure can be simply an overlap 442 of the thin strap material of which the legs are made, secured by a rivet 444. Turned-up lugs 446 on the lower legs define the position of the unfolded configuration at each pivot.

From the foregoing the combination of versatility and simplicity of the invention will be apparent. The hands of the user can be independently used, one hand being free to drop the handle and support the user, if necessary. It is evident that the transparent portion can be stiff enough for self-support so that it can be hung on the arm to free the other hand.

Further, in use with an electric tool such a reciprocating saw it is evident that the tool guard will press against frame tubing and slide the unit along rather than cut into it.

This invention is not to be construed as limited to the particular forms disclosed herein, since these are to be regarded as illustrative rather than restrictive. It is, therefore, to be understood that the invention may be practiced within the scope of the claims otherwise than as specifically described.

What is claimed and desired to be protected by United States Letters Patent is:

1. In an article of apparel for protecting a user from debris resultant to overhead operation of a tool held in a first hand of a user including a sleeve having upper and lower portions, means for retaining the sleeve lower portion around a first hand of a user, and means for spreading the sleeve upper portion around a said overhead operation, the improvement comprising: the sleeve having means for providing protective visual access through an area thereof to said overhead operation, including a transparent flexible upper part extending substantially around the sleeve; the sleeve having means for preventing debris from being blown out of the sleeve as result of motion of said a user's first hand during said overhead operation of a tool including the sleeve having a lower filter-type flexible porous part extending substantially around the sleeve, said pores having proportion for passage of air while retaining debris within the sleeve; and said means for spreading the sleeve including a handle having orientation for grasping by a second hand of a user.

2. In an article as recited in claim 1, the means for spreading including a planar frame having attachment to the handle, the handle orientation including a downward angle from said attachment for providing hand clearance at said overhead, and means on the planar frame for cushioning the top of the planar frame against a said overhead.

3. In an article as recited in claim 2, said handle and planar frame forming in plan view a generally pear-shape.

4. In an article as recited in claim 2, said handle and frame comprising separate parts and said attachment comprising a pivotal attachment for folding.

5. In an article as recited in claim 1, said means for retaining the sleeve lower portion including a resilient member located for constrictively closing an opening for said a user's first hand in the sleeve lower portion, and the sleeve porous part including a substantially full size downward continuation of the sleeve upper portion and of sufficient length that the bottom-most part thereof forms a pocket for debris.

* * * * *